(12) United States Patent
Suriye et al.

(10) Patent No.: US 10,143,997 B2
(45) Date of Patent: Dec. 4, 2018

(54) STABILIZED RHENIUM-BASED HETEROGENEOUS CATALYST AND USE THEREOF

(71) Applicant: SCG Chemicals Co., Ltd., Bangkok (TH)

(72) Inventors: Kongkiat Suriye, Samutprakarn (TH); Amnart Jantharasuk, Nakhon si Thammarat (TH); Weena Phongsawat, Chanthaburi (TH)

(73) Assignee: SCG Chemicals Co., Ltd., Bangkok (TH)

( * ) Notice: Subject to any disclaimer, the term of this patent is extended or adjusted under 35 U.S.C. 154(b) by 0 days.

(21) Appl. No.: 15/524,026

(22) PCT Filed: Aug. 4, 2015

(86) PCT No.: PCT/TH2015/000049
§ 371 (c)(1),
(2) Date: May 3, 2017

(87) PCT Pub. No.: WO2016/022080
PCT Pub. Date: Feb. 11, 2016

(65) Prior Publication Data
US 2017/0291161 A1    Oct. 12, 2017

(30) Foreign Application Priority Data
Aug. 5, 2014    (EP) .................................. 14179779

(51) Int. Cl.
*C07C 6/02*    (2006.01)
*C07C 11/06*    (2006.01)
(Continued)

(52) U.S. Cl.
CPC ................ *B01J 23/36* (2013.01); *C07C 6/04* (2013.01); *B01J 2231/54* (2013.01); *C07C 2521/04* (2013.01); *C07C 2521/06* (2013.01); *C07C 2521/16* (2013.01); *C07C 2521/18* (2013.01); *C07C 2523/08* (2013.01);
(Continued)

(58) Field of Classification Search
CPC .... C07C 6/04; C07C 6/02; C07C 6/00; C07C 2523/36
See application file for complete search history.

(56) References Cited

U.S. PATENT DOCUMENTS

| 4,508,850 A * | 4/1985 | Banks ...................... B01J 21/04 502/351 |
| 5,877,365 A | 3/1999 | Chodorge et al. |

(Continued)

FOREIGN PATENT DOCUMENTS

EP    0273817 A1    7/1988

OTHER PUBLICATIONS

International Search Report and Written Opinion PCT/TH2015/000049 dated Oct. 8, 2015.

*Primary Examiner* — Youngsul Jeong
(74) *Attorney, Agent, or Firm* — Banner & Witcoff, Ltd.

(57) ABSTRACT

The present invention relates to a stabilized rhenium-based heterogeneous catalyst, obtainable by a process comprising contacting a rhenium-based heterogeneous catalyst with a stabilizing agent at a temperature in a range from 0-100° C., the stabilizing agent comprising an aliphatic hydrocarbon compound and use thereof.

20 Claims, 4 Drawing Sheets

(51) Int. Cl.
*B01J 23/36* (2006.01)
*C07C 6/04* (2006.01)

(52) U.S. Cl.
CPC ...... *C07C 2523/14* (2013.01); *C07C 2523/36* (2013.01); *C07C 2527/04* (2013.01); *C07C 2527/22* (2013.01); *C07C 2529/06* (2013.01); *C07C 2531/12* (2013.01); *Y02P 20/52* (2015.11)

(56) References Cited

U.S. PATENT DOCUMENTS

| | | |
|---|---|---|
| 5,898,091 A | 4/1999 | Chodorge et al. |
| 6,075,173 A | 6/2000 | Chodorge et al. |
| 6,235,958 B1 * | 5/2001 | Commereuc ............ B01J 23/36 585/644 |
| 6,277,781 B1 | 8/2001 | Commereuc et al. |

* cited by examiner

STABILIZED RHENIUM-BASED HETEROGENEOUS CATALYST AND USE THEREOF

CROSS-REFERENCE TO RELATED APPLICATIONS

This application is a U.S. National Stage application under 35 U.S.C. § 371 of International Application PCT/TH2015/000049 (published as WO 2016/022080 A1), filed Aug. 4, 2015, which claims the benefit of priority to EP 14179779.5, filed Aug. 5, 2014. Benefit of the filing date of each of these prior applications is hereby claimed. Each of these prior applications is hereby incorporated by reference in its entirety.

FIELD OF INVENTION

The present invention relates to a stabilized rhenium-based heterogeneous catalyst and a process for producing an olefin compound using said catalyst.

BACKGROUND OF INVENTION

Metathesis reaction is used for the conversion of olefins. In the metathesis reaction, olefins of the same or different kinds are reacted with each other to yield olefins having different structures, for example, metathesis of ethylene and butene to propylene and metathesis of butene to pentene and propylene.

Various catalysts have been developed for olefins metathesis. Among these, catalysts having an oxide of molybdenum, tungsten and rhenium supported on a high surface area carrier receive highest industrial interest.

Molybdenum- and tungsten-based catalysts are more widely used in industrial metathesis processes due to their higher tolerance to catalyst poisonous substances and less expensive cost. However, they are known to be less active comparing to rhenium and therefore require higher temperature, typically above 100° C., and preferably above 200° C., in order to achieve a desired activity. The higher temperature employed conveniently results in reduced selectivity due to occurrence of side reactions, such as olefin isomerization and oligomerization.

Rhenium is highly active in olefins metathesis. It can be operated in a significantly lower temperature range. However, its rapid deactivation is a major drawback.

European patent application EP 027817 A1 discloses an olefin metathesis process carrying out in the presence of a rhenium catalyst in a moving bed reaction zone wherein the catalyst is then reoxidized in a connected regeneration zone. This enables the process to be continuously operated despite the high deactivation rate of the rhenium catalyst. However, a moving bed process is much more complex and energy consuming, and therefore is normally less desirable in industrial applications, especially comparing to a fixed bed system.

U.S. Pat. No. 6,277,781 B1 discloses a method for reducing deactivation rate of a rhenium-based metathesis catalyst, the method comprising treating the catalyst at a temperature of more than 750° C. in a hydrocarbon-containing stream, e.g. a methane stream, in the presence of hydrogen, and activating under a non-reduction atmosphere at a temperature in the range of 400-1,000° C. prior to carrying out metathesis reaction and it is preferred that the catalyst contains some amount of cesium.

Therefore, it is an object of the present invention to provide a stabilized rhenium-based heterogeneous catalyst overcoming the drawbacks of the prior art, in particular displaying improved reaction stability and tolerance to poisonous substances.

It is a further object of the present invention to provide a stabilized rhenium-based heterogeneous catalyst which allows use of the catalyst in a fixed bed reactor.

Also another object of the present invention is to provide an improved process for production of an olefin compound in which the operating cycle time is increased.

SUMMARY OF INVENTION

The above objects are achieved by a stabilized rhenium-based heterogeneous catalyst and a process for preparation thereof, wherein the process comprises contacting a rhenium-based heterogeneous catalyst with a stabilizing agent at low temperatures.

More particularly, this object is achieved by a stabilized rhenium-based heterogeneous catalyst obtainable by a process comprising contacting a rhenium-based heterogeneous catalyst with a stabilizing agent at the temperature in a range from 0-100° C., the stabilizing agent comprising an aliphatic hydrocarbon compound.

DETAILED DESCRIPTION OF INVENTION

The rhenium-based heterogeneous catalyst according to the present invention contains rhenium in a form of elemental metal and/or at least one rhenium compound, for example rhenium oxide, rhenium hydride, rhenium sulfide, rhenium carbide or any combination thereof, deposited on a solid support.

The solid support on which the rhenium compound is deposited can be selected from many porous materials. In one embodiment, the solid support is selected from the group consisting of $Al_2O_3$, $Ga_2O_3$, $SiO_2$, $GeO_2$, $TiO_2$, $ZrO_2$, $SnO_2$, aluminosilicate, activated carbon, hydrotalcite anionic clays, or mixtures thereof, preferably $Al_2O_3$, $SiO_2$, or a mixture thereof. Suitable solid supports typically have a specific surface area of 10 to 500 $m^2/g$, preferably 100 to 400 $m^2/g$.

The rhenium-based heterogeneous catalyst can be prepared by methods known in the art for preparation of a heterogeneous catalyst. In general cases, preparation of the rhenium-based heterogeneous catalyst is carried out by a) impregnating a solid support with a solution of a rhenium compound and b) subsequently drying and calcining the support which has been impregnated.

Proportion of rhenium presents on the catalyst is usually in a range of 0.01% to 20% by weight of the total catalyst. The rhenium-based heterogeneous catalyst in the present invention may be subjected to further modification to incorporate additional components as appropriate to customarily adjust property of the catalyst. For example, the catalyst may further contain a compound of a transition metal such as palladium or platinum to provide activity for hydrogenation reaction or a compound of an alkaline or alkaline earth metal to provide activity for isomerization reaction.

The rhenium-based heterogeneous catalyst is contacted with a stabilizing agent to prepare a stabilized rhenium-based heterogeneous catalyst. In an embodiment, the stabilizing agent comprises an aliphatic hydrocarbon compound, preferably an aliphatic hydrocarbon compound containing 2 to 6 carbon atoms, more preferably an alkane or alkene compound containing 2 to 4 carbon atoms. In terms of the present invention, a compound comprising n carbon atoms shall be labeled as Cn compound. That is, for example, a C2 aliphatic hydrocarbon compound may be ethane, ethene or ethyne. In preferred embodiments, the stabilizing agent is selected from the group consisting of ethane, ethylene, propane, propylene, butane, butene or mixtures thereof.

Conditions, in which contacting a stabilizing agent with a rhenium-based heterogeneous catalyst is carried out, need to be carefully chosen in order to enable stabilization of the catalyst. It is preferred that contacting is at a temperature is in a range from 0 to 100° C., preferably 10 to 60° C., more preferably 20 to 40° C. In a preferred embodiment, the contacting condition includes a pressure is in a range from 1 to 50 bars, preferably 10 to 30 bars. Higher temperature and/or more severe contacting conditions tend to lead to formation of carbonaceous substances over the rhenium active sites resulting in the catalyst deactivation.

The stabilized rhenium-based heterogeneous catalyst after being treated with the stabilizing agent displays altered hydrophobic property of the rhenium active sites due to the adsorbed stabilizing agent. This causes the catalyst to be more selective to the olefin feedstock and less active to catalyst poisonous substances, particularly oxygenate substances.

The process according to the present invention is simple, does not require severe operating condition and surprisingly results in a stabilized rhenium-based heterogeneous catalyst with improved reaction stability and tolerance to poisonous substances.

The stabilized rhenium-based heterogeneous catalyst can be beneficially employed in several reaction processes in which rhenium can provide appropriate reaction activity, for example, olefin epoxidation, alcohol oxidation, and in particular metathesis reactions.

The present invention also concerns a process for production of an olefin compound using the stabilized rhenium-based heterogeneous catalyst obtained by the stabilizing process described above. The process comprises contacting the stabilized rhenium-based heterogeneous catalyst with an olefin feed stream.

The object of the present invention is further achieved by a process for preparing an olefin hydrocarbon compound comprising contacting a stabilized rhenium-based heterogeneous catalyst according to the invention with an olefin feed stream, wherein the olefin feed stream comprises at least one olefin selected from C2 to C12 olefin or mixtures thereof, and contacting is carried out at a temperature in the range from 0 to 300° C., preferably 10 to 100° C., more preferably 20 to 60° C.

Contacting the olefin feed stream with the stabilized rhenium-based heterogeneous catalyst is to be carried at an enabling condition for transforming the feed stream to a desired olefin product. Preferably, the enabling condition includes a temperature in a range from 0° C. to 100° C., more preferably 10° C. to 80° C., most preferably 20° C. to 60° C.

The olefin feed stream capable of being converted to an olefin compound product in the presence of the stabilized rhenium-based heterogeneous catalyst according to the present invention can be at least one olefin with 2 to 12 carbon atoms, preferably 2 to 6 carbon atoms. The olefin feed stream can contain a single species of olefin which can be made to react on itself, for example in an auto-metathesis reaction, to produce a different olefin. In a more general case, the olefin feed stream can contain more than one species of olefin wherein they can be made to react with each other to produce a different olefin.

In a specific embodiment of the present invention, the process for production of an olefin compound comprises contacting the stabilized rhenium-based heterogeneous catalyst obtained by the process according to the present invention with an olefin feed stream comprising a mixture of C2 and C4 linear olefin and/or a mixture of C2 and C5 linear olefin.

In an embodiment wherein the olefin feed stream comprises C4 linear olefin, it is possible that the C4 linear olefin is provided in a form of a mixture of C4 linear olefin, non-linear olefin, diolefin, and paraffin. Such mixture is usually referred to as "C4-cut" which is a stream normally produced from a thermal cracking process for olefin production. It is often beneficial to subject the C4-cut to a pre-treatment process prior to entering the process according to the present invention. The pre-treatment process can include transformation and separation of certain components and left with only the component which will actively transform to a desired olefin product upon contacting with the stabilized rhenium-based heterogeneous catalyst according to the present invention. Examples of C4 cut pretreatment process can be found in U.S. Pat. No. 5,877,365, U.S. Pat. No. 5,898,091, and U.S. Pat. No. 6,075,173.

More particularly, the present invention concerns a process for production of an olefin compound comprising contacting the stabilized rhenium-based heterogeneous catalyst obtained by the process according to the present invention with an olefin feed stream comprises an olefin selected from C2 to C12 olefin, preferably C2 to C6 linear olefin, and mixtures thereof at an enabling temperature for conversion of the olefin feed stream to a desired olefin product, preferably in a range from 0 to 300° C., more preferably 10 to 100° C., most preferred 20 to 60° C.

Even more particularly, the present invention concerns a process for production of propylene, the process comprises contacting the stabilized rhenium-based heterogeneous catalyst obtained by the process according to the present invention with an olefin feed stream comprising a mixture of C2 and C4 olefins or a mixture of C2 and C5 olefins at a temperature from 10 to 100° C.

In some embodiments, the process for production of an olefin hydrocarbon is carried out at a pressure in a range from 1 to 50 bar and a WHSV (weight hourly space velocity) in a range from 0.1 to 100 $h^{-1}$ The catalyst employed in the process for production of an olefin hydrocarbon according to the present invention generally gradually deactivates over time and therefore regeneration of the catalyst is periodically required. Any known technique for heterogeneous catalyst regeneration can be employed without limitation. The regeneration process generally involves desorption and burning off any adsorbed carbonaceous species with simultaneous re-calcination under flowing of dilute air at a temperature in a range from 300-800° C. The regeneration enables at least partially, or even totally in some cases, recovery of the catalyst's catalytic performance. In some embodiments, the process for preparation of a stabilized rhenium-based heterogeneous catalyst according to the present invention can be conveniently performed immediately after the catalyst regeneration process and before the next reaction cycle.

Preferably, the process for production of an olefin hydrocarbon according to the present invention is carried out in a fixed bed reactor.

Finally, the object of this invention is achieved by use of a stabilized rhenium-based heterogeneous catalyst according to the invention for catalyzing a hydrocarbon conversion reaction.

The stabilized catalyst prepared by the process according to the present invention enable the process for production of an olefin compound, preferably by metathesis reaction, to be operated with longer operating cycle between each regeneration. For example in an implementation of the present invention with a process for production of propylene from a feed stream comprising a mixture of C4-cut and ethylene, the stabilized rhenium-based heterogeneous catalyst shows approximately 3 times longer operating cycle length comparing to the rhenium-based heterogeneous catalyst prepared by a conventional preparation method without stabilization according to the present invention. In some embodiments, contacting the stabilizing agent with the rhenium-based heterogeneous catalyst according to this invention is carried out by providing the rhenium-based heterogeneous catalyst in a fixed bed reactor and flowing a fluid stream comprising the stabilizing agent through the provided catalyst bed and then it is subsequently followed by contacting the stabilized catalyst with an olefin feed stream at reaction condition.

The following examples illustrate embodiments of the present invention without limiting its scope.

Examples

Several catalysts were prepared according to the invention and compared with catalyst prepared according to the prior art. The catalysts were composed as follows:

Catalyst A (comparative) is a non-stabilized rhenium oxide on gamma-alumina support catalyst.

Catalysts B, C, D, and E are rhenium oxide on gamma-alumina support catalysts according to the invention stabilized by flowing a stabilizing gas through a fixed bed of the catalyst at a stabilizing temperature.

Catalysts F, G, and H (comparative) are rhenium oxide on gamma-alumina support catalysts pretreated by flowing a stabilizing gas through a fixed bed of the catalyst at a high temperature.

Catalysts A to H were subjected to metathesis reaction tests. The tests were carried out by flowing 12 g/h of a C4 olefins mixture and 120 sccm of ethylene through a fixed bed of 6 grams of the catalyst sample at a temperature 30° C. and a pressure 20 bar. Details and results of the tests are shown in Table 1

TABLE 1

| Test No. | Catalyst | Oxygenate content in feed stream (ppm) | Stabilizing gas | Stabilizing (Pretreatment) temperature (° C.) | 2-butene conversion (%) 2 h | 2-butene conversion (%) 50 h | 2-butene conversion (%) 100 h | Propylene selectivity (%) 2 h | Propylene selectivity (%) 50 h | Propylene selectivity (%) 100 h |
|---|---|---|---|---|---|---|---|---|---|---|
| 1 | A | 0.50 | None | None | 89.8 | 70.4 | 15.0 | 97.1 | 88.8 | N/A |
| 2 | A | 0.65 | None | None | 87.4 | 45.2 | N/A | 96.4 | 71.6 | N/A |
| 3 | B | 0.65 | Propylene | 30 | 85.3 | 51.4 | 32.0 | 98.1 | 81.1 | 71.9 |
| 4 | C | 0.65 | Propane | 30 | 91.0 | 52.6 | N/A | 97.2 | 86.2 | N/A |
| 5 | D | 0.65 | Ethane | 30 | 89.7 | 55.5 | 41.6 | 97.1 | 86.4 | 81.8 |
| 6 | E | 0.65 | Ethylene | 30 | 88.7 | 69.9 | 56.2 | 98.4 | 88.0 | 81.6 |
| 7 | F | 0.65 | Ethylene | 120 | 80.7 | $53.7^a$ | N/A | 95.6 | $86.7^a$ | N/A |
| 8 | G | 0.65 | Ethylene | 150 | 12.8 | — | — | 68.4 | — | — |
| 9 | H | 0.65 | Ethylene | 300 | 7.0 | — | — | 0 | — | — |

Note:
(1) N/A means data not available
(2) $X^a$ are data measured at time on stream 29 hours It can be observed from Tests No. 1 and 2 that content of oxygenate substance in the feed stream obviously effect deactivation of the catalyst. In Test No. 3, 4, 5, and 6, the result shows that the use of that stabilized rhenium-based heterogeneous catalyst according to the present invention significantly reduces the effect of the oxygenate substance.

Also, in Tests No. 3, 4, 5, and 6, it can be seen that various hydrocarbon compounds can be utilized as a stabilizing agent in the present invention.

In Tests No. 7, 8, and 9, it can be seen that a higher temperature does not results in a stabilized catalyst in terms of the invention. On the contrary, it significantly has adverse effect on performance of the catalyst.

Figure 1:
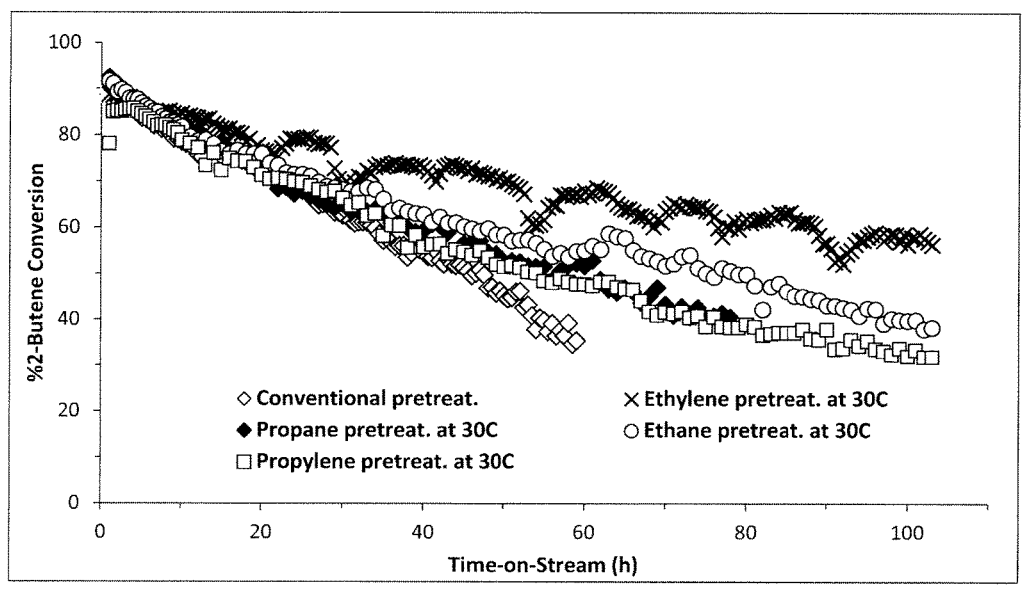
FIG. 1 illustrates the effect of stabilizing agent on 2-butene conversion.
Figure 2:
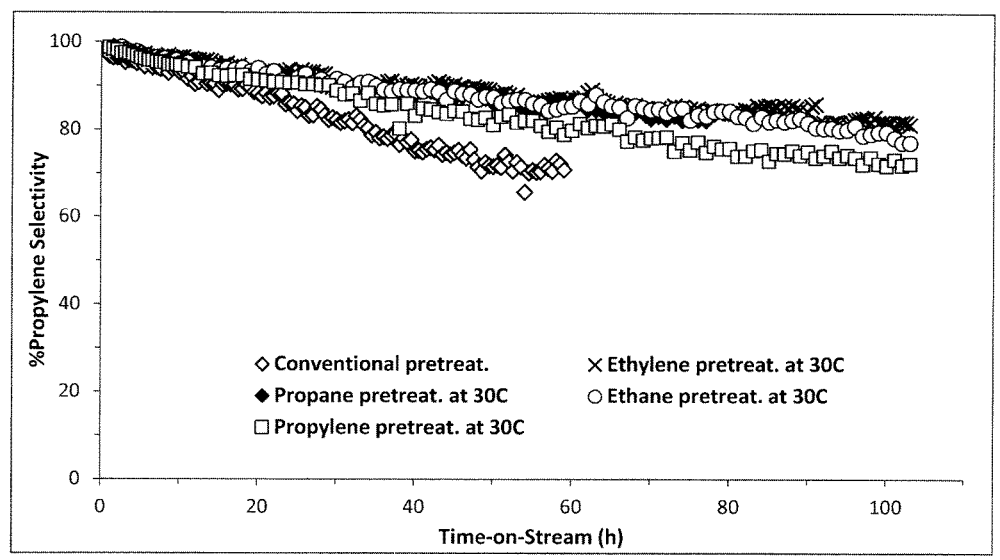
FIG. 2 illustrates the effect of stabilizing agent on propylene selectivity.

Comparative results of using catalysts stabilized by different stabilizing agents and non-stabilized catalyst (marked as "conventional pretreat") in metathesis reaction of ethylene and mixed C4 streams to produce propylene are illustrated in FIG. 1 and FIG. 2.

Figure 3:
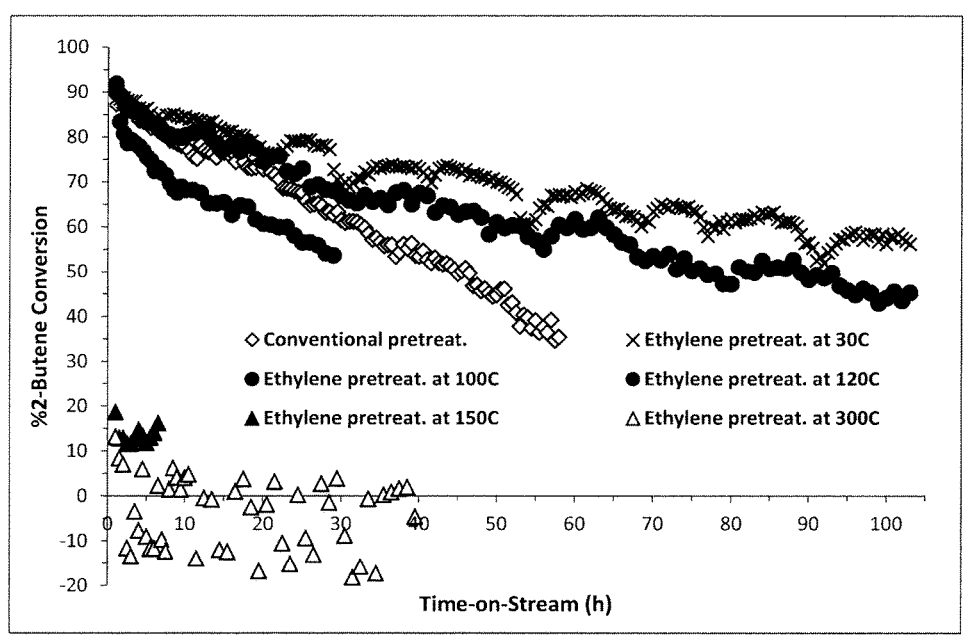
FIG. 3 illustrates the effect of stabilizing temperature on 2-butene conversion.
Figure 4:
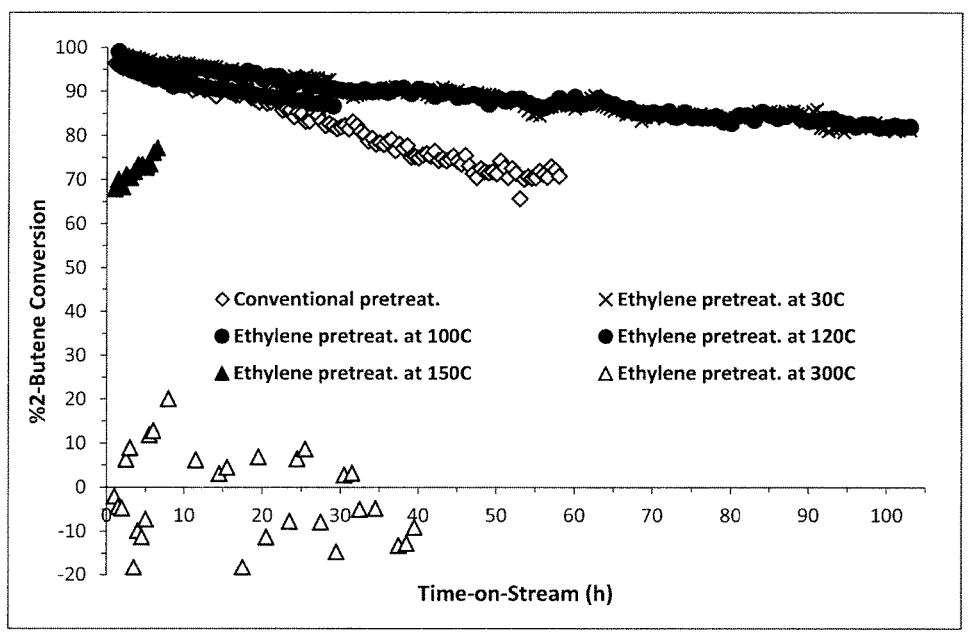
FIG. 4 illustrates the effect of stabilizing temperature on propylene selectivity.

Comparative results of using catalysts stabilized by a stabilizing agent at different temperatures and non-stabilized catalysts (marked as "convention pretreat") in metathesis reaction of ethylene and mixed C4 streams to produce propylene are illustrated in FIG. 3 and FIG. 4.

The features disclosed in the foregoing description, in the claims and/or in the accompanying drawings may, both separately and in any combination thereof, be material for realizing the invention in diverse forms.

BEST MODE FOR CARRYING OUT THE INVENTION

The best mode of practicing the invention is as described in the above Detailed Description of Invention.

The invention claimed is:
1. A process for preparing an olefin hydrocarbon compound, the process comprising:
  contacting, in the absence of an olefin feed stream, a rhenium-based heterogeneous catalyst with a stabiliz- ing agent comprising an aliphatic hydrocarbon selected from the group consisting of ethane, ethylene, propane, and propylene, to provide a stabilized rhenium-based heterogeneous catalyst, followed by reacting the olefin feed stream in the presence of the stabilized rhenium-based heterogeneous catalyst to obtain the olefin hydrocarbon compound, wherein the olefin feed stream comprises a C4 olefin, a C5 olefin, or a mixture thereof, and wherein the reacting is carried out at a temperature in a range from 0 to 300° C.

2. The process according to claim 1, wherein the contacting is carried out at a temperature from 0° C. to 100° C. to provide the stabilized rhenium-based heterogeneous catalyst.

3. The process according to claim 1, wherein the contacting is carried out at a temperature from 10° C. to 60° C. to provide the stabilized rhenium-based heterogeneous catalyst.

4. The process according to claim 1, wherein the reacting of the olefin feed stream in the presence of the stabilized rhenium-based heterogeneous catalyst is carried out in a fixed bed reactor.

5. The process of claim 1, wherein the olefin feed stream comprises (i) ethylene and a C4 linear olefin, (ii) ethylene and a C5 linear olefin, or (iii) ethylene and both C4 and C5 linear olefins.

6. The process according to claim 3, wherein the contacting is carried out at a temperature from 20 to 40° C.

7. The process of claim 1, wherein the rhenium-based heterogeneous catalyst comprises elemental rhenium or a rhenium compound, wherein rhenium is present in an amount from 0.01% to 20% by weight of the catalyst.

8. The process of claim 1, wherein the rhenium-based heterogeneous catalyst comprises elemental rhenium or a rhenium compound, disposed on a solid support comprising $Al_2O_3$, $Ga_2O_3$, $SiO_2$, $GeO_2$, $TiO_2$, $ZrO_2$, $SnO_2$, aluminosilicate, activated carbon, hydrotalcite, an anionic clay, or a mixture thereof.

9. The process of claim 8, wherein the solid support comprises $Al_2O_3$ or $SiO_2$.

10. The process of claim 8, wherein the rhenium-based heterogeneous catalyst comprises elemental rhenium, rhenium oxide, rhenium hydride, rhenium sulfide, or rhenium carbide.

11. The process of claim 1, wherein the contacting provides the stabilized rhenium-based heterogeneous catalyst with increased conversion stability and/or increased selectivity to the olefin hydrocarbon compound, relative to performing the reacting alone.

12. The process of claim 11, wherein the olefin feed stream comprises oxygenated compounds.

13. The process of claim 1, wherein the olefin hydrocarbon compound is propylene that is obtained from an olefin metathesis reaction, with ethylene, of the C4 olefin and/or the C5 olefin of the olefin feed stream.

14. The process of claim 1, wherein the rhenium-based heterogeneous catalyst has been subjected to regeneration, prior to the contacting.

15. A process for preparing an olefin hydrocarbon compound, the process comprising:

contacting, in the absence of an olefin feed stream, a rhenium-based heterogeneous catalyst with a flow of a stabilizing gas comprising an aliphatic hydrocarbon compound selected from the group consisting of ethane, ethylene, propane, and propylene, to provide a stabilized rhenium-based heterogeneous catalyst, followed by reacting the olefin feed stream in the presence of the stabilized rhenium-based heterogeneous catalyst to obtain the olefin hydrocarbon compound, wherein the olefin feed stream comprises at least one olefin selected from the group consisting of C4 to C12 olefins, and wherein the reacting is carried out at a temperature in a range from 0 to 300° C.

16. The process of claim 15, wherein the olefin feed stream comprises (i) a C2 olefin and a C4 olefin or (ii) a C2 olefin and a C5 olefin.

17. The process of claim 15, wherein the olefin feed stream comprises oxygenated compounds.

18. A process for preparing an olefin hydrocarbon compound, the process comprising:

contacting a rhenium-based heterogeneous catalyst with a stabilizing agent comprising ethane or propane, to provide a stabilized rhenium-based heterogeneous catalyst, followed by reacting an olefin feed stream in the presence of the stabilized rhenium-based heterogeneous catalyst to obtain the olefin hydrocarbon compound, wherein the olefin feed stream comprises at least one olefin selected from the group consisting of C2 to C12 olefins, and wherein the reacting is carried out at a temperature in a range from 0 to 300° C.

19. The process of claim 18, wherein the contacting provides the stabilized rhenium-based heterogeneous catalyst with increased conversion stability and/or increased selectivity to the olefin hydrocarbon compound, relative to performing the reacting alone.

20. The process of claim 18, wherein the rhenium-based heterogeneous catalyst has been subjected to regeneration, prior to the contacting.

* * * * *